United States Patent [19]
Allan et al.

[11] Patent Number: 6,013,845
[45] Date of Patent: Jan. 11, 2000

[54] FIXED BED REACTOR PACKING

[75] Inventors: Edgar Donald Allan, Katy; Raymond Lawrence June, Houston; YeMon Chen, Sugar Land; Robert Lawrence Blackbourn, Houston, all of Tex.

[73] Assignee: Shell Oil Company, Houston, Tex.

[21] Appl. No.: 08/820,790

[22] Filed: Mar. 19, 1997

Related U.S. Application Data

[60] Provisional application No. 60/013,831, Mar. 21, 1996.

[51] Int. Cl.[7] .................................................. C07C 39/16
[52] U.S. Cl. ............................................................ 568/728
[58] Field of Search .................................... 568/722, 727, 568/728; 422/211

[56] References Cited

U.S. PATENT DOCUMENTS

| | | |
|---|---|---|
| 3,673,228 | 6/1972 | Harris et al. . |
| 4,032,407 | 6/1977 | Scott et al. . |
| 4,053,522 | 10/1977 | McClure et al. . |
| 4,215,011 | 7/1980 | Smith, Jr. . |
| 4,250,052 | 2/1981 | Smith, Jr. . |
| 4,385,983 | 5/1983 | Rosenthal et al. . |
| 4,847,016 | 7/1989 | Henkel et al. . |
| 5,019,669 | 5/1991 | Adams et al. . |
| 5,080,871 | 1/1992 | Adams et al. . |
| 5,118,872 | 6/1992 | Smith, Jr. et al. . |
| 5,118,873 | 6/1992 | Smith, Jr. . |
| 5,244,929 | 9/1993 | Gottlieb et al. . |
| 5,248,836 | 9/1993 | Bakshi et al. . |
| 5,275,790 | 1/1994 | Buchholz et al. . |
| 5,302,774 | 4/1994 | Bayer . |
| 5,315,042 | 5/1994 | Cipullo et al. . |
| 5,395,857 | 3/1995 | Berg et al. . |
| 5,414,151 | 5/1995 | Pressman . |
| 5,430,204 | 7/1995 | Manogue et al. . |
| 5,463,140 | 10/1995 | Wehmeyer et al. . |
| 5,463,157 | 10/1995 | Hendricksen et al. . |

FOREIGN PATENT DOCUMENTS

| | | |
|---|---|---|
| 324080 | 7/1989 | European Pat. Off. . |
| 522920 | 1/1993 | European Pat. Off. . |
| 630878 | 12/1994 | European Pat. Off. . |
| 774325 | 5/1957 | United Kingdom . |

OTHER PUBLICATIONS

Encl. Search Report.

*Primary Examiner*—Michael L. Shippen
*Attorney, Agent, or Firm*—Todd F. Volyn

[57] ABSTRACT

A reactor system for conducting chemical reactions is presented in which a reactor is operated in an upflow mode with a fixed bed catalyst and randomly distributed reactor packing therein. The reactor system and the process in which it is used exhibit plug flow behavior and are amenable to employing lightly crosslinked ion exchange resin catalysts.

2 Claims, 2 Drawing Sheets

FIXED BED REACTOR PACKING

FIELD OF THE INVENTION

This application claims the benefit of the filing of U.S. Provisional patent application Ser. No. 60/013,831 filed on Mar. 21, 1996. This invention is related to chemical reactor design and use.

BACKGROUND

Ensuring that reacting species achieve optimal physical contact can be among the most difficult challenges in chemical reactor design. If done improperly, numerous undesired byproducts and an abundance of unreacted reactants can seriously erode the economics of the system. The reactor type (i.e., batch, plug flow, stirred tank, or combinations thereof), reactant and product diffusion, pressure effects, and other factors must all be considered in selecting or fabricating a reactor system best suited for use in a given reaction.

Reactor residence time and reaction conditions such as pressure and temperature impact the percentage of atomic or molecular collisions and thus affect yield, throughput, and selectivity. Backmixing is another phenomenon which can contribute to further reaction of the reactor products. Backmixing is the mixing of a molecule or intermediate which has been present in the reactor for a given length of time with a molecule or intermediate which has been present in the reactor for a lesser period of time. The amount of backmixing that occurs can be related to reactor geometry and type; fluid dynamics of the reactants, intermediates and products produced in the reactor; and other factors. In some processes optimizing the production of products by adjusting these parameters is easily understood and straightforward.

The employment of finely tuned catalyst can complicate reactor design and reaction control. For example, U.S. Pat. No. 5,395,857 proposes that in the production of bisphenol A (BPA) in a downflow reactor, the degree of crosslinking of certain ion exchange resin catalysts directly affects the physical performance of the process as well as the reactivity and selectivity of the reaction. There the inventors found that the deleterious hydraulic impact attributable to catalyst particle shape and the compression of the catalyst bed due to pressure can be ameliorated by using a two layer catalyst in which at least one of the layers comprises a ion exchange resin catalyst which exhibits a 2% or lower degree of crosslinking. The process is directed to increasing the volume and time yield of fixed bed reactors. It would be further desirable to employ an ion exchange resin catalyst such as the one proposed in U.S. Pat. No. 5,395,857 because of the greater selectivity and activity offered by such catalysts and because resin based catalysts with greater degrees of crosslinking tend to desulphonate more readily.

It is sometimes desirable or necessary to conduct reactions in the upflow mode. For example, in downflow processes the potential for catalyst bed collapse at high flow rates because of the low degree of crosslinking and the effects that this has on the physical properties of the catalyst must be considered. Increased byproduct production attributable to longer residence times must be also be considered. Thus, it would be desirable to operate the reactor in the upflow mode to allow the resin bed to fluidize instead of collapsing and to take advantage of possible selectivity improvements.

We have also found that if one could effectively operate in the upflow mode it would be possible to employ reactors of much smaller size to achieve comparable throughput and selectivity improvement relative to those used in downflow reactors due to significant reduction or elimination of pressure drop through the reactor. Unfortunately, fluidization in the upflow process leads to back-mixing of the catalyst and reactor feed. This reduced plug flow characteristic reduces per pass conversion of reactants to products and can lead to wasteful catalyst entrainment known to be a problem with upflow reactors.

Chemical process technology could benefit generally if it were possible to improve catalyst and fluid behavior within reactor systems. More particularly, chemical processes conducted in upflow reactor systems could prove advantageous if the aforementioned problems were resolved.

SUMMARY OF THE INVENTION

This invention is a reactor system which improves the per pass yield of product by increasing the plug flow character of the reactor and/or reducing backmixing in the reactor. The reactor system comprises a chemical reactor, fluidized bed catalyst and reactor packing randomly oriented with respect to the catalyst.

In one embodiment of this invention, the reactor system is an upflow reactor system for the production of BPA wherein the catalyst is a 2% crosslinked sulfonic acid resin.

In another embodiment of this invention, the packing comprises high open area, high void volume corrosion resistant articles such as pall rings.

In yet another embodiment of this invention a process for the production of BPA is presented comprising reacting phenol and acetone in an upflow fixed bed chemical reactor having therein 2% crosslinked sulfonic acid ion exchange resin catalyst and randomly distributed reactor packing.

DETAILED DESCRIPTION OF THE INVENTION

The reactor system and process of this invention are best understood by referring to the Figures.

Figure 1:
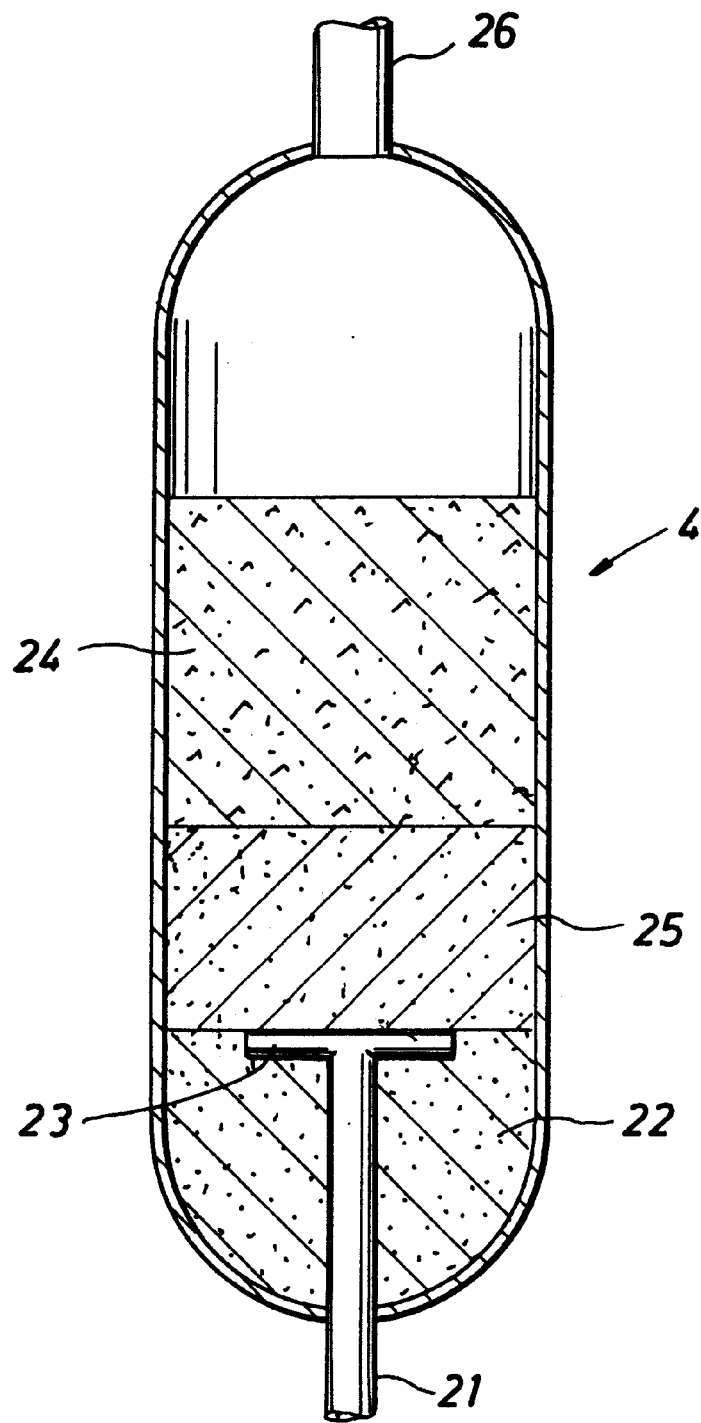
FIG. 1 is a cross sectional view of a reactor system utilized this invention.

FIG. 1 shows the reactor system of this invention. Reactant is introduced into reactor 4 through reactant vessel 21. Any type of reactor used to react reactants in the presence of catalyst is generally amenable to practicing this invention. However, cylindrical reactors are preferred for their simplicity.

Vessel 21 can comprise tubing, pipes, jets, or other common means for introducing reactants into the reaction zone of a reactor. Reactants are typically distributed into the reaction zone by passage through a distribution lateral 23 which can be a perforated pipe, sparging arm, or other similar or conventional means for transferring fluids. Preferably, the bottom portion of the reactor is filled with aggregate 22. The amount of such aggregate is not critical to this invention. However, sufficient aggregate should be present to provide support to the reactor internals and disperse the flow of reactants throughout the interior of the reactor. This aggregate can comprise any material which will not easily fluidize and is essentially inert to the reactants and products produced in the reactor. Preferably, this aggregate is comprised of silica sand, ceramic balls, or a combination of both. In the most preferred embodiment wherein acetone (dimethyl ketone, "DMK") and phenol are reacted to produce BPA, the aggregate comprises a first portion of silica sand and a second portion of ceramic balls (½", ¼", and ⅛") lying atop the silica sand.

The reactor 4, is charged with packing 24 and catalyst 25. Preferably, between about 10 and about 50% volume of the reactor are taken up by the catalyst (determined when dry). However, as one skilled in the art will appreciate, this is greatly dependent on the parameters of the reaction in question and particularly the properties, structure, and composition of the catalyst involved. In the most preferred embodiment of this invention wherein DMK and phenol are reacted to form BPA, between about 15 and 40% volume of the reactor are occupied by catalyst. Such processes often employ reactors with total internal volumes of between about 2,000 and 10,000 ft$^3$. Reactor packing 24 is randomly distributed atop the catalyst as is more fully described below.

It is most preferred that in the reactor system of this invention the catalytic agents are sulfonated aromatic resins comprising hydrocarbon polymers having a plurality of pendant sulfonic acid groups. These are typically 2 or 4% divinyl benzene crosslinked. Catalysts having a 2% or lower degree of cross linking are most preferred. Poly (styrenedivinylbenzene) copolymer, and sulfonated phenol-formaldehyde resins have utility in this regard. Sulfonated resin catalysts commercially available as "AMBERLITE A-32" brand catalyst from Rohm and Haas Chemical Company, Inc. and "K1131" brand catalyst from Bayer Chemical Company are examples of such suitable catalysts. The exchange capacity of the acidic resin is preferably at least about 2.0 meq. H$^+$/gram of dry resin. Ranges from 3.0 to about 5.5 meq H$^+$/gram of dry resin are most preferred.

Cocatalysts may also be used in the most preferred processes of this invention. These are preferably comprised of alkyl mercaptans such as methyl mercaptan, ethyl mercaptan, propyl mercaptan. Methyl mercaptan is presently the preferred cocatalyst. It is also possible to employ a catalyst as set forth above with a fixed mercaptan group ionically or covalently bound thereto. Such catalysts with fixed mercaptan groups typically have about 1–25 mol-% of the sulfonic acid groups covered with species containing alkyl-SH.

Sufficient reactor packing 24 is randomly distributed among the catalyst 25. In the preferred embodiment of this invention in which BPA is manufactured, between about 25 and 75% of the reactor volume (measured under phenol-wet resin catalyst conditions prior to reactant entry) are occupied by randomly distributed catalyst packing. It is most preferred that between about 30 to 60% of the volume is so occupied under the same conditions. Any method for randomly distributing the packing material may be used. The easiest and most preferred method is to simply place the packing materials into the reactor and add catalyst to the reactor to distribute within the packing void volumes. Alternatively, another method is to simply place the packing materials atop the catalyst at the time that the maintenance or shutdown of the reactor is undertaken. Packing is dumped into the reactor and allowed to form a random arrangement as is known, for example, in the art of preparing packed distillation columns.

Reactor packing materials having a high void volume and high open area are preferred. Further, the packing should be inert to the reactants, intermediates, products, catalysts, and any other materials that may be present in the reactor with the packing. Corrosion resistant metals such as stainless steel are preferred in large part for this reason. Plastic packing materials are not generally preferred because they are not generally compatible with the materials present in the reactor and because most are not dense enough to sink in the fluidized bed. Examples of suitable packing materials are Pall rings, Berl saddles, Intalox packing, Tellerette packing, Hyperfill packing, Stedman packing, Sulzer packing, and Rasching rings, all of which are described by J. R. Fair et. al in Perry's Chemical Engineers' Handbook (6 ed., 1984) in Section 18 and/or by K. E. Porter et al. in Chemistry and Engineering (Feb. 4, 1967) at pages 182–188. Pall rings are most preferred since they have the greatest amount void volume (>90%) and open area.

Pall rings are generally commercially available in five-eighths, 1 inch, 1.5 inch, 2 inch, and 3 inch sizes. These rings are stamped, preferably from stainless steel, and formed into open-ended cylinders of approximately equal and outer diameter and height. The sides of the cylinders are comprised of holes formed by punching material from the sides to create tongues extending into the center of the cylinder. Except for the holes and tongues, the packing is similar to Raschig rings.

Reaction products, intermediates for further processing, and unreacted reactant exit the reactor 4 through vessel 25 which is similar to vessel 21.

Figure 2:
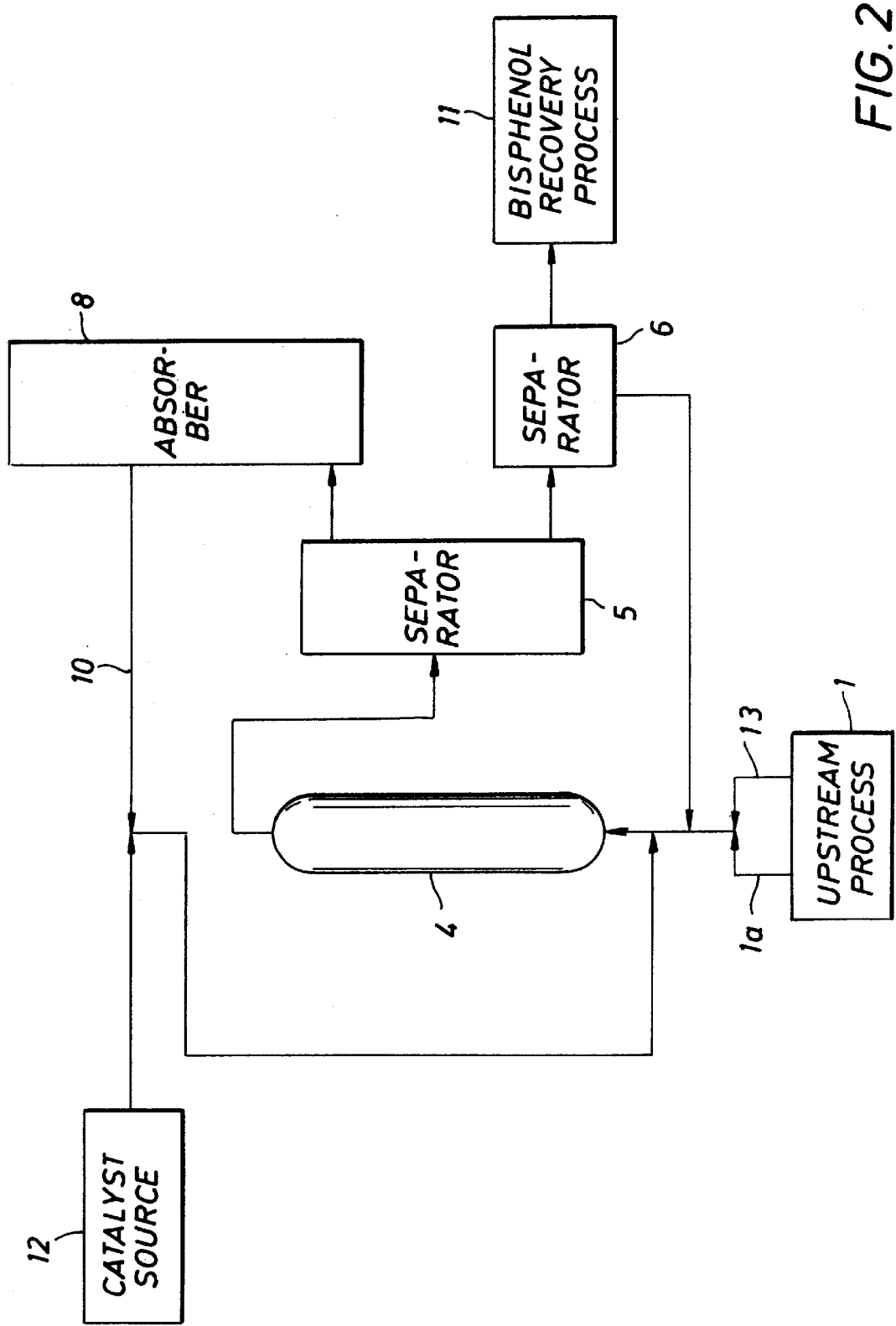
FIG. 2 is a schematic diagram of a process according to this invention.

FIG. 2 further describes the process of this invention as it may be applied to the production of bisphenols from ketones and phenols. Upstream process 1 produces ketones and phenols (such as DMK and phenol). One such upstream process is the cleavage of cumene hydroperoxide. It is also possible to employ as reactant "on purpose" DMK produced by the oxidation of isopropyl alcohol. Upstream process 1 is also understood to be the bisphenol reactant source.

Two different streams of reactants, a ketone stream 1a, and a phenol stream 13 are withdrawn from upstream process 1. The ketone stream is, together with phenol stream 13, fed into reactor 4. Feed stream volumes flowing into reactor 4 can be up to about 200,000 lbs per hour although, as one skilled in the art will readily appreciate, the feed rate is dependent upon the conditions in which the reaction is carried out.

Reactor 4 can be a single reactor system as described above or can be a series of reactor systems as described above operated in series or parallel. The reactor(s) 4 are operated in the upflow configuration at temperatures between about 40° C. and 95° C. and pressures between about 1 and 5 atmospheres. Reactor 4 is also charged with aggregate, a 2% crosslinked sulfonic acidic ion exchange resin catalyst and reactor packing such as Pall rings as discussed above. Finally, reactor 4 is also charged with free mercaptan cocatalyst of the type discussed above. Alternatively, reactor 4 is charged with catalyst having a fixed mercaptan group or a mulitlayer catalyst bed is formed wherein one layer is catalyst free of mercaptan and another layer is catalyst having fixed mercaptan. In the free cocatalyst process, cocatalyst can be originally fed into the reactor from a cocatalyst source 12.

The reactants in reactor 4 react to form bisphenol (BPA when the reactants are DMK and phenol) and leave the reactor 4 as a product stream comprising the bisphenol, unreacted reactants, cocatalyst, and minor amounts of other materials. When the reaction commences the catalyst bed is fluidized but backmixing of catalyst and reactor feed is minimized such that the reactor 4 operates in a substantially plug flow manner.

The product stream is fed into the separator 5 which can be any conventional method for separating such materials. Distillation is generally the simplest and most preferred method. However, other well known methods can be used independently or in combination with distillation to comprise this separation process.

When the separation is done as a distillation, the tops products will comprise the cocatalyst and a small amount of other materials. These tops products are fed to the cocatalyst absorber column 8 which comprises a column filled with phenol. In the cocatalyst absorber column 8, cocatalyst is absorbed from the rest of the tops products of separator 5 and is returned to the reactor via a cocatalyst return line 10.

The bisphenol product, bisphenol isomers, phenol, and a small amount of various impurities are removed from separator 5 as a bottoms product. This bottoms product is fed to a further separator 6. Crystallization is the preferred method of bisphenol separation but any method which can be used to separate bisphenol from the mother liquor can be used depending upon the desired degree of purity of the bisphenol product. Once separated, the mother liquor comprising phenol and bisphenol isomers is returned to the reactor 4 as reactant 13.

Bisphenol separated from mother liquor in separator 6 can then be sent to yet further separations and purifiers such as the bisphenol recovery process 11. This can be particularly important where very pure product is required as where BPA is produced for use in the subsequent production of polycarbonates. Generally, such further separations can be beneficially conducted using techniques such as recrystallization.

Conducting this process essentially enables one to undertake an upflow process with a fluidized bed catalyst in which backmixing is eliminated relative to prior art processes. This results in converting the process to one exhibiting predominantly plug flow behavior. The improvement in throughput is about 20% (by weight of products). Improvements in reaction selectivity also result from the practice of this invention.

The invention is further described in the following non-limiting examples.

EXAMPLE 1 (Comparative)

A 2% crosslinked sulphonated resin catalyst commercially available as "A-32 AMBERLITE" brand resin from Rohm and Haas, Inc.was charged placed in the bottom of a 19" internal diameter acrylic column (height of 6') such that the catalyst occupied about 33% volume of the column (determined prior to flow). Water (at ambient temperature) was flushed through the system in an upflow manner at a rate of between about 6 and 18 gallons per minute. Under these conditions the flow character of phenol and DMK in the reactor were replicated.

The column was constructed of polymethylmethacrylate (PMMA) so that flow characteristic could be visibly observed. The catalyst bed fluidized. Back mixing of the resin was visible and pervasive as the amber color catalyst was seen forming a plume and rotating in a circular manner.

EXAMPLE 2

The process of Example 1 was repeated except that 2 inch pall rings were first randomly distributed among the catalyst such that about 60% volume of the reactor (determined prior to water flow) was occupied by packing.

As water flowed through the simulated reactor, the catalyst bed fluidized but no plume formed. Further, small zones of mixing were observed throughout the entire volume. This was characteristic of a series of small staged continuously stirred tank reactors and is indicative of an overall plug flow behavior.

We claim as our invention:

1. A process for producing bisphenols comprising introducing phenol and ketone into the reactor system comprising:
    (a) an upflow chemical reactor;
    (b) a sulfonated aromatic fixed bed ion exchange resin catalyst having no greater than 2% degree of crosslinking charged in said reactor; and
    (c) packing randomly distributed within said reactor;
in an upflow mode, reacting the reactants in said reactor systems, and recovering the products thereof.

2. The process of claim 1 wherein said packing is comprised of pall rings.

* * * * *